(12) United States Patent
Anderson et al.

(10) Patent No.: US 8,954,144 B2
(45) Date of Patent: Feb. 10, 2015

(54) HYBRID CLUSTERED NEURAL INTERFACE SYSTEM

(75) Inventors: David Anderson, Ann Arbor, MI (US); Daryl R. Kipke, Dexter, MI (US); Jamille Hetke, Brooklyn, MI (US); Rio J. Vetter, Augusta, MI (US); Kc Kong, Ann Arbor, MI (US); John Seymour, Ann Arbor, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 248 days.

(21) Appl. No.: 13/524,989

(22) Filed: Jun. 15, 2012

(65) Prior Publication Data

US 2012/0323288 A1 Dec. 20, 2012

Related U.S. Application Data

(60) Provisional application No. 61/497,905, filed on Jun. 16, 2011.

(51) Int. Cl.
*A61N 1/00* (2006.01)
*A61N 1/05* (2006.01)

(52) U.S. Cl.
CPC .................................. *A61N 1/0531* (2013.01)
USPC ............................................................. 607/3

(58) Field of Classification Search
CPC ........................................................ A61N 1/36
USPC ............................................................. 607/2, 3
See application file for complete search history.

(56) References Cited

U.S. PATENT DOCUMENTS

2004/0121528 A1* 6/2004 Krulevitch et al. ........... 438/166
2011/0093052 A1* 4/2011 Anderson et al. ............. 607/116

* cited by examiner

*Primary Examiner* — Christopher D Koharski
*Assistant Examiner* — Nadia A Mahmood
(74) *Attorney, Agent, or Firm* — Michael F. Scalise (57) ABSTRACT

An apparatus comprises a flexible substrate. The flexible substrate includes a first substrate surface, a surface electrode array that includes a plurality of electrodes disposed on the first substrate surface, one or more flexible neural probes substantially orthogonal to the first substrate surface and insertable into biological tissue, and a penetrating electrode array that includes a plurality of electrodes formed on the one or more flexible neural probes, wherein electrodes of the surface electrode array and the penetrating electrode array are configured to one or both of receive a neural signal from a neural signal source and provide electrical stimulation energy to a neural stimulation target.

45 Claims, 6 Drawing Sheets

HYBRID CLUSTERED NEURAL INTERFACE SYSTEM

CROSS-REFERENCE TO RELATED APPLICATION

This application claims the benefit of priority, under 35 U.S.C. §119(e), to U.S. Provisional Application No. 61/497,905, filed on Jun. 16, 2011, which is incorporated herein by reference in its entirety.

BACKGROUND

Neural interface systems are typically implantable devices that are placed into biological tissue (e.g., brain or other neural tissue) and have the ability to record and/or stimulate the tissue through electrode sites. For example, neural interface systems may be strategically positioned in the brain (such as the cerebral cortex or in intracortical tissue) to record neural signals. However, there are several issues with current conventional neural interface systems. In long-term applications, conventional implantable neural interface systems have less-than-optimal reliability and reduced longevity due to degradation of the implanted device over time, thereby reducing the usability of the device. Furthermore, many of these implanted neural interface systems can cause potentially significant tissue trauma to the patient. The tissue trauma can cause neural signal degradation due to both acute and chronic tissue responses to the implant, such as local neuronal loss, increased tissue encapsulation, and other reactions to tissue trauma caused by the implantation. The acute and chronic tissue responses can negatively impact the usability of the neural device once implanted in the tissue. Thus, there is a need in the neural interface field to create a new and useful hybrid clustered neural interface system.

OVERVIEW

This document relates generally to systems, devices, and methods to sense neural signal sources and provide therapy to neural stimulation sites. An apparatus example includes a flexible substrate. The flexible substrate includes a first substrate surface, a surface electrode array that includes a plurality of electrodes disposed on the first substrate surface, one or more flexible neural probes substantially orthogonal to the first substrate surface and insertable into biological tissue, and a penetrating electrode array that includes a plurality of electrodes formed on the one or more flexible neural probes, wherein electrodes of the surface electrode array and the penetrating electrode array are configured to one or both of receive a neural signal from a neural signal source and provide electrical stimulation energy to a neural stimulation target.

This section is intended to provide an overview of subject matter of the present patent application. It is not intended to provide an exclusive or exhaustive explanation of the invention. The detailed description is included to provide further information about the present patent application.

DETAILED DESCRIPTION

Figures 1A, 1B:
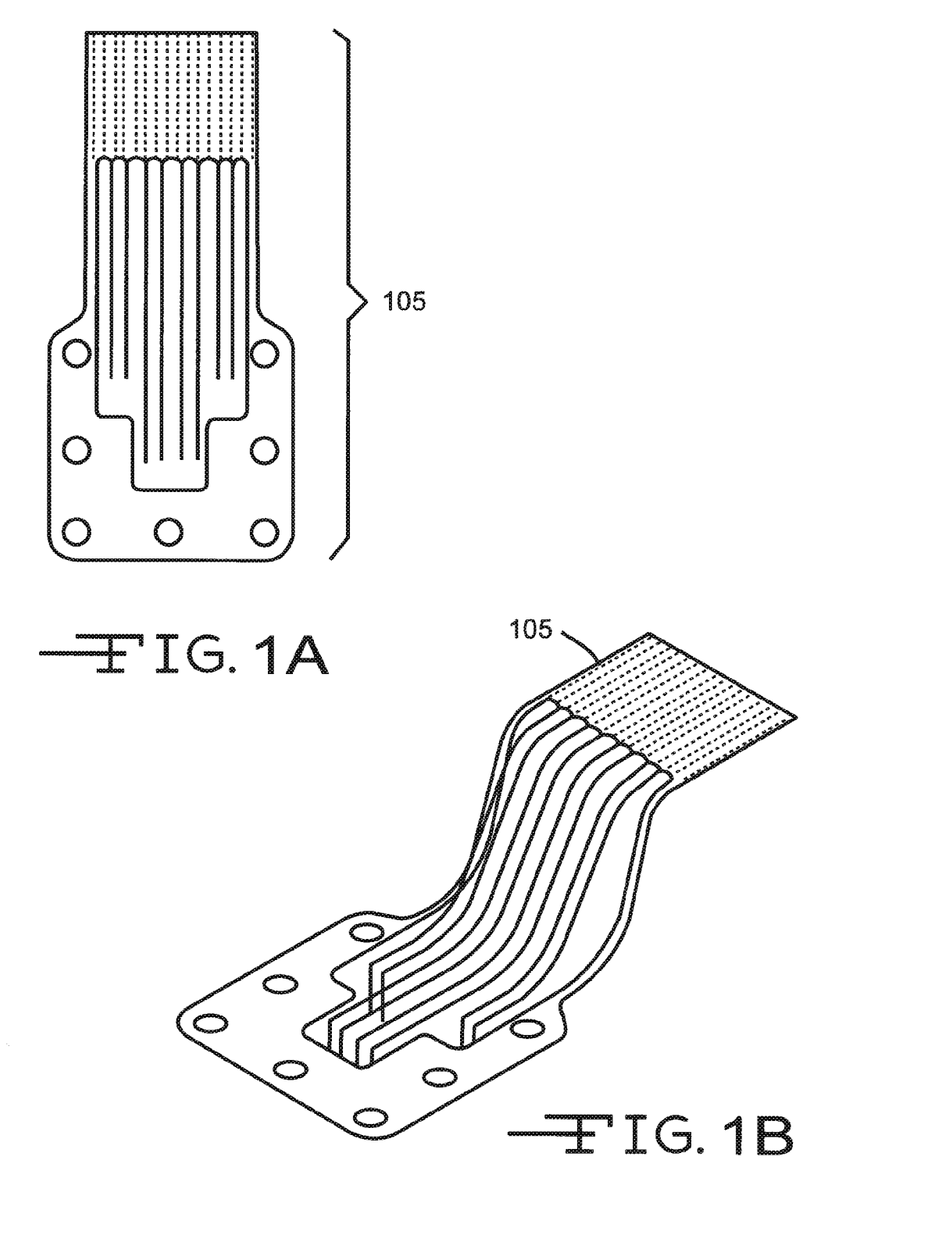
FIGS. 1A and 1B illustrate an example of a hybrid clustered neural interface system.

FIG. 1A and FIG. 1B illustrate an example of a hybrid clustered neural interface system. The system includes a flexible substrate 105. The flexible substrate 105 includes a surface electrode array and a penetrating electrode array.

Figure 2:
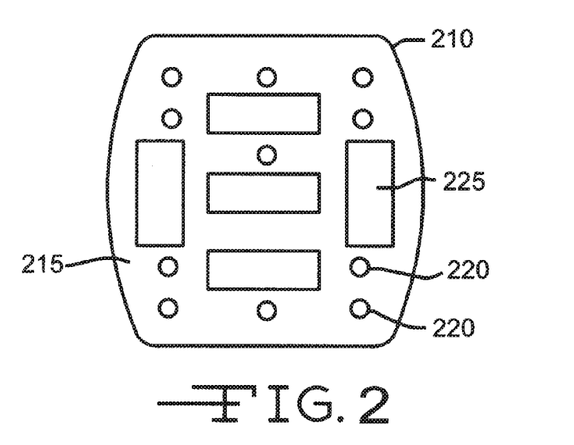
FIG. 2 is a diagram of an example of a surface electrode array.

FIG. 2 is a diagram of an example of a surface electrode array 210. The surface electrode array 210 of the hybrid neural interface system functions to receive and record neural signals on the surface of the tissue. The example shows a first surface 215 of the flexible substrate and the surface electrode array 210 includes a plurality of electrodes 220 or electrode sites disposed on the first substrate surface. The example also shows one more apertures 225 that can be included in the flexible substrate. The apertures 225, pores, or other features can be included that deliver drugs and/or other fluids to the surface tissue.

Figures 3, 4:
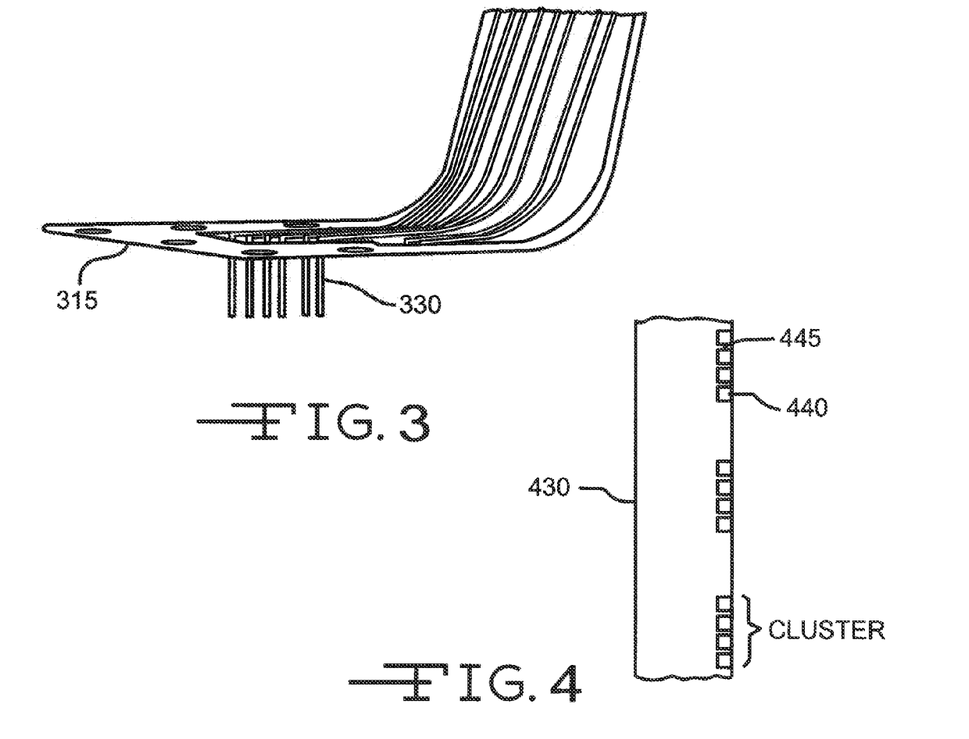
FIG. 3 is another illustration of an example of a hybrid clustered neural interface system.
FIG. 4 is an illustration of an example of a portion of flexible neural probe.

FIG. 3 is another illustration of the example of the hybrid clustered neural interface system. The system includes one or more flexible neural probes 330 substantially orthogonal to the first substrate surface 315 and insertable into biological tissue. The penetrating electrode array includes a plurality of electrodes formed on the flexible neural probes.

FIG. 4 is an illustration of an example of a portion of flexible neural probe 430. The example illustrates electrodes 440 or electrode sites separated by an insulating material 445 formed on the flexible neural probe 430. The electrodes of the surface electrode array and the penetrating electrode array are configured to one or both of receive a neural signal from a neural signal source and to provide electrical stimulation energy to a neural stimulation target.

The electrodes can include gold or any other suitable conductive material, and can be electrically isolated from one another, such as with a thin-film polymer insulation material on the neural probe or substrate and interspersed between the electrodes, or with any other suitable insulation material. The electrodes may be roughened, such as to reduce electrical impedance, and may include any suitable modifications. The electrodes may be formed on the probe substrate by any suitable semiconductor manufacturing process or other manufacturing steps.

The electrodes of one or both of the surface electrode array and the penetrating electrode array can be distributed to substantially align to a target neural cluster. The target neural cluster can include a plurality of one or both of neural signal sources and neural stimulation targets.

For instance, the electrodes on each flexible neural probe can include "clusters" of recording sites arranged on the edge of the neural probe. Within each cluster of electrode sites on the neural probes, the edge electrode sites can be spaced to achieve optimal signal redundancy for maximum reliability and control of information flow. In particular, closely spaced clustering of electrode sites can enable overlapping groups of neurons to be sensed and recorded across a cluster.

The surface electrode array can be configured to interface with the outermost surface of the cerebral cortex and the penetrating electrode array, and the penetrating electrode array can be configured to be implanted in intracortical tissue, although both the surface electrode array and the penetrating electrode array may be configured to interface with or be implanted in any suitable neural or other tissue.

Figure 5:
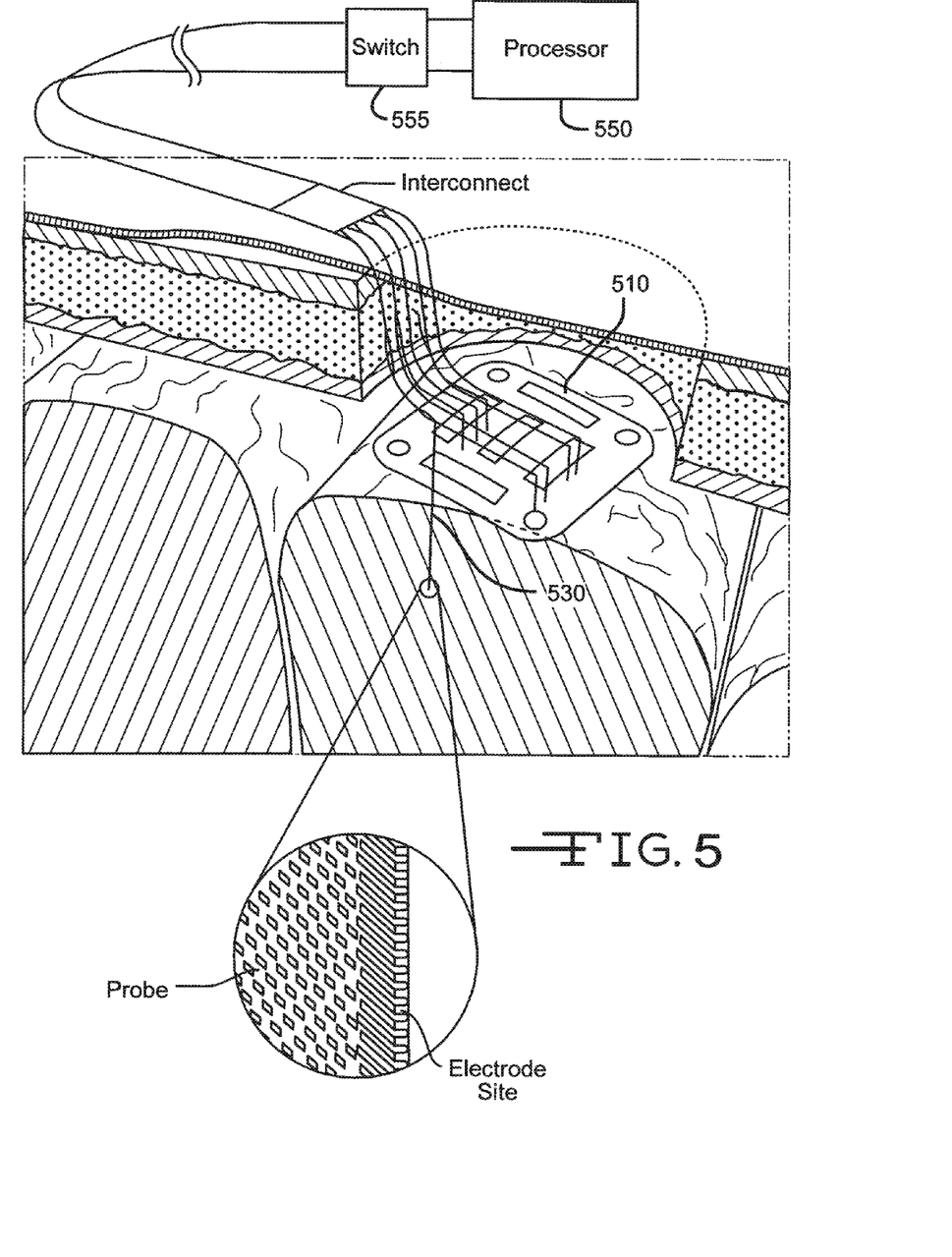
FIG. 5 shows an illustration of an implanted hybrid clustered neural interface system.

FIG. 5 shows an illustration of an implanted hybrid clustered neural interface system. The system includes a surface electrode array 510 and a penetrating electrode array formed penetrating neural probes 530. The electrodes in the surface electrode array and the penetrating electrode array can be precisely distributed within targeted cortical areas to best sample desired information, such as motor-control information, and/or the overall layout of the surface and penetrating electrode arrays is preferably custom configured to specific cortical areas and signal modalities required for particular applications (e.g. cortical prosthesis applications). Furthermore, the surface and/or penetrating electrode arrays can be multi-scale and multi-modal electrode arrays that are configurable to tailor the neural interface system to meet specific desired signal reliability, information flow, and longevity requirements. In other words, the hybrid clustered neural interface system can be designed to closely match the layout and fine scale structure of the electrode array to the distribution and density of neural signal sources in the targeted cortical areas to optimize fit and function of the system to particular target tissue, without degradation of the system over time.

The hybrid clustered neural interface system can be a multi-modal, multi-unit neural interface system that is highly customizable. A spacing of the electrodes of one or both of the surface electrode array and the penetrating electrode array can be scaled to a spacing of a target neural cluster. The scale of the spacing facilitates separate sensing of neural signal sources of the target neural cluster and facilitates separate stimulation of neural stimulation targets of the target neural cluster.

FIG. 5 shows the system connected to a processor circuit 550. The processor circuit 550 can include a microprocessor, digital signal processor, application specific integrated circuit (ASIC) or other type of processor. The processor circuit 550 may facilitate the recording of data and may control stimulation to the electrode sites. The system can include a switch circuit 555 electrically coupled to the plurality of electrodes. The switch circuit 555 can selectively activate (e.g., by decoding) a subset of the plurality of electrodes for one or both of separate sensing of a neural signal source and separate stimulation of a neural stimulation target. The selective activation can result from an external command generated by the processor circuit 550 or a user.

The clustered electrode sites can be configured with engineered redundancy to optimally match the sensor distribution to the information content in a noisy cortical environment, such that the combination of the surface and penetrating electrode arrays may be leveraged to significantly increase system-level interface reliability and information flow.

Returning to FIGS. 1A and 1B, the flexible substrate 105 can be substantially planar and configured to lie on the surface of the tissue to which it interfaces, although alternatively the substrate may be curved or have any suitable shape to conform with the surface of tissue. The substrate 105 can be made of a flexible, high-strength, and long-lasting material, although the substrate may additionally and/or alternatively include any suitable material. In some examples, the flexible substrate 105 has a sub-cellular thickness, such as a thickness of approximately 5 µm or less. The sub-cellular thickness may help reduce adverse tissue reactions and increase longevity of the surface electrode array. The substrate area may vary depending on the specific application, and can range between tens of micrometers (µm) to centimeters (cm).

In some examples, the substrate includes a flexible, thin-film polymer microelectromechanical systems (MEMS) structure, and the features of the flexible substrate can be formed using photolithography. In certain examples, a first flexible thin-film substrate is used to form the surface components (e.g., the surface electrode array) and a second flexible thin-film substrate is used to form the penetrating components (e.g., the neural probes). In certain examples, the flexible substrate includes a flexible thin-film substrate and is monolithic (e.g., both the surface components and the penetrating components are formed from the same thin-film substrate). In certain examples, the flexible substrate includes a thin-film substrate mounted on a flexible backing. In certain examples, the flexible substrate includes a thin-film substrate mounted on a temporary backing that is more rigid than the thin-film substrate. The temporary backing can provide stiffness as an aid for insertion in the biological tissue. The temporary backing can then be removed after insertion into the tissue.

As explained previously herein, the flexible substrate 105 can include one or more apertures. The apertures can be configured by shape and size to deliver a fluid to an interface of the flexible substrate and the biological tissue. The apertures can be configured to deliver light to the interface of the flexible substrate and the biological tissue, such as by a fiber optic channel.

As shown in FIG. 3, the substrate can include one or more apertures through which the neural probes 330 of the penetrating electrode array pass and penetrate the tissue. A particular aperture may be relatively large to accommodate more than one flexible neural probe or to accommodate flexibility in positioning of a neural probe relative to the substrate, or a particular aperture may be relatively large to accommodate and precisely position a single neural probe relative to the substrate. The number of apertures in the substrate may be less than, equal to, or greater than the number of neural probes in the penetrating electrode array. Alternatively, the substrate may lack such neural probe apertures. The neural probes of the penetrating electrode array penetrate the tissue arranged along the perimeter of the substrate.

The electrode sites of the surface electrode array and the penetrating electrode array can be disposed on the substrate such that the electrode sites are adjacent to the tissue surface. The electrode sites preferably include one or more recording electrode sites that record local field potentials (LFPs) and/or electrocorticography (ECoG) signals from the surface tissue. In some embodiments, the electrode sites may additionally and/or alternatively include one or more stimulating electrodes that provide electrical stimulation, such as for therapeutic applications.

The penetrating electrode array functions to receive and record neural signals within the tissue (e.g. the penetrating electrode array is an intracortical array that measures signals below the cortex of the brain). The penetrating electrode array can be arranged proximate to the surface electrode array and can include at least one neural probe configured to penetrate the tissue. Each flexible neural probe can include a probe substrate and a respective plurality of electrode sites disposed on the probe substrate.

Each flexible neural probe is preferably substantially planar, although at least a portion of the neural probes may additionally and/or alternatively include cylindrical probes or probes of any suitable shape. Similar to the surface electrode array, each neural probe is preferably made of a flexible, high-strength, and long-lasting material, although the neural probe may additionally and/or alternatively include any suitable material. Each neural probe preferably has a subcellular thickness and/or width, which may help reduce adverse tissue reactions and increase longevity of the surface electrode array. In one embodiment, each neural probe may have an open architecture design with strategically placed perforations that anchor the device in the tissue and improve stability, and may locally improve molecular diffusion and the cellular environment.

The flexible substrate can include a plurality of electrical conductors in electrical contact with the electrodes of the surface electrode array and the electrodes of the penetrating array, wherein the electrical conductors can be used to perform one or both of receiving signals from the electrodes and providing electrical stimulation energy to the electrodes.

As explained previously herein, the flexible substrate can be monolithic and the surface substrate of the surface electrode array can be formed from the same thin-film as the flexible neural probes. The flexible substrate can be fabricated to include serpentine conductive traces. If the flexible substrate is made from a flexible yet strong material (e.g., polyimide), a trace can then be cut and folded to form a flexible neural probe. The flexible neural probes can be foldable to change the position of the penetrating electrode array relative to the position of the surface electrode array.

Figure 6:
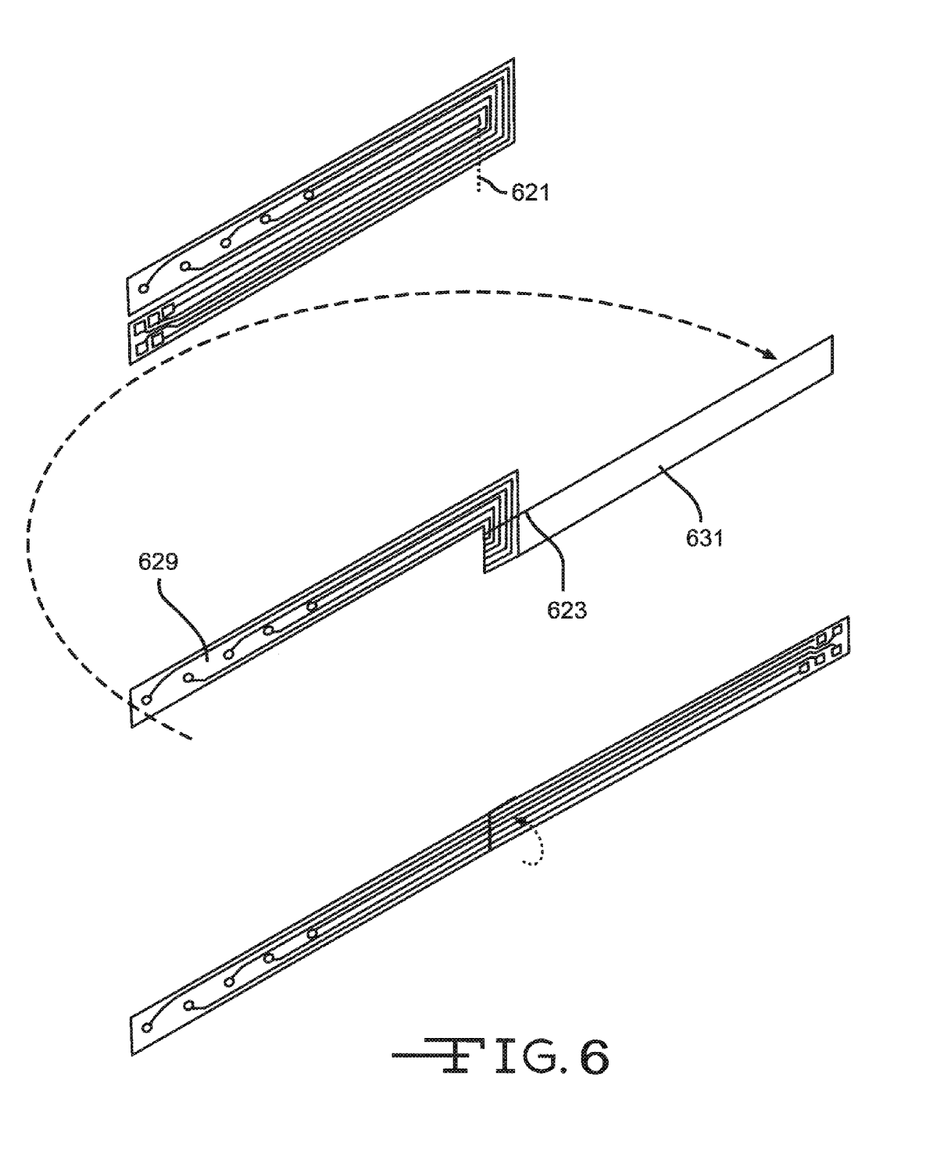
FIG. 6 shows an example of a folding process to form a flexible neural probe.

FIG. 6 shows an example of a process including one or both of bending and folding a portion of a flexible substrate to form a flexible neural probe. A portion of the flexible substrate used to form a neural probe is illustrated. To perform the fold, one segment 629 is stabilized while the other segment 631 is flipped under and then crimped down at a fold line 621. The crimping process can be performed using a polished surface such as a glass slide or metal block. The second fold is performed by flipping the second segment 631 up and then crimping the device at the fold line 623 to form the final straight shape. Different folding can result in flexible neural probes of different lengths. A formed neural probe can be mounted to a carrier to provide stiffness to penetrate tissue or the probe can be pointed and have sufficient stiffness to penetrate tissue without the need for a carrier. In some examples, the carrier includes a lumen.

The penetrating electrode array may include multiple neural probes that are distributed across the area of the surface electrode array, and extend away (e.g. approximately perpendicularly, or at any suitable angle) from the surface electrode array through apertures in the electrode array.

The neural probes may penetrate the tissue at locations around the perimeter of the surface electrode array. The distribution of neural probes in the system may be regular such as in a grid pattern, or irregular such as a pattern that is customized for particular tissue structures. Furthermore, the neural probes may be arranged such that the electrode sites are distributed in a two-dimensional or three-dimensional pattern. The neural probes may be of approximately equal lengths or may have different lengths. The electrode sites disposed on each probe substrate in the penetrating electrode array function to record reliable single-unit and/or multi-unit neural activity in the tissue.

As explained previously herein, each plurality of electrode sites of the neural probes preferably include one or more "clusters" of recording electrode sites, although the plurality of electrode sites on a neural probe may additionally and/or alternatively include stimulation electrode sites. Each cluster may have any particular number of electrodes. For instance, a cluster may include a stereotrode (2 closely spaced electrode sites), a tetrode (4 closely spaced electrode sites), an octrode (8 closely spaced electrode sites), or a polytrode, for various strategies in recording quality and accuracy.

In some examples, the penetrating electrode array includes approximately 10-300 separate recording electrode sites distributed among the clusters, although the penetrating electrode array may include any suitable number of recording sites. In some examples, as shown in FIG. 4, the electrode sites are preferably arranged on the edge of the neural probe. However, in alternative embodiments some or all of the electrode sites may be arranged in the center of the neural probe, or on a location besides the edge of the neural probe. The edge electrode sites on a sub-cellular probe may further contribute to reducing adverse tissue response to the neural interface system, such as by allowing increased neuronal density in surrounding tissue and less cellular encapsulation around the electrode sites. Within each cluster of electrode sites on the neural probes, the edge electrode sites may be spaced to achieve optimal signal redundancy for maximum reliability and control of information flow, and to match the distribution of neural sources within the target tissue. In certain examples, at least one of the clusters preferably senses and records neural signals from overlapping groups of neurons, and the degree to which the overlapping groups of neurons are sensed preferably depends at least partially on the spacing between the electrode sites within a cluster and/or the spacing between clusters.

The spacing, or pitch, of the electrode sites on the edge of a neural probe may be physically set (e.g. during manufacture) or functionally set and/or modulated during analysis after implantation in the tissue, by turning on and/or off selected channels (that is, signal collection from particular selected electrode sites), thereby altering and preferably optimizing the sensor redundancy in the neural interface system for a particular tissue environment or application. In a preferred embodiment, the pitch of the electrode sites is between approximately 15-40 μm, although the pitch may be any suitable distance. Furthermore, the distance between the clusters may be any suitable distance.

Figure 7:
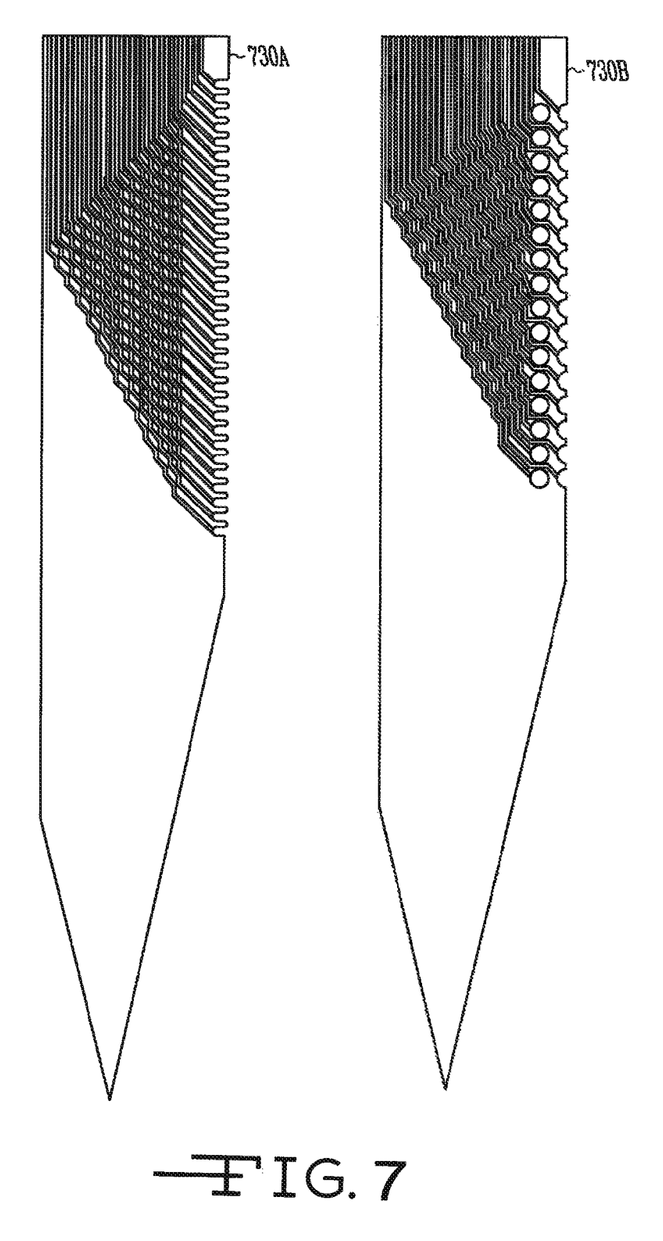
FIG. 7 shows portions of examples of flexible neural probes.

FIG. 7 shows portions of examples of flexible neural probes and closely spaced electrode contacts of the probes. The Figure shows a flexible neural probe 730A having a linear arrangement of electrode sites and a flexible neural probe 730B having a bi-linear arrangement of electrode sites. However, it should be noted that the electrode site arrangement can be formed into any two-dimensional (2D) cluster of electrode sites. The example probes shown are substantially planar, but in some examples a flexible neural probe is cylindrical in shape.

A flexible neural probe may further include at least one fluid channel configured to deliver fluid to at least one of the first substrate surface or a flexible neural probe. In certain examples, the fluid channel can include a lumen passing along the length of the probe or a portion of the probe, such as for distributing fluid to the surrounding tissue and/or for receiving a single channel microelectrode. The flexible substrate may include at least one fluid channel to deliver fluid to the neural probe. In some examples, the flexible substrate includes at least one optical channel configured to deliver light to one or both of a substrate surface and a neural probe.

As explained previously herein regarding FIG. 5, the system may include a processor circuit 550 that functions to analyze signals from the electrode sites to resolve near simultaneous events and improve reliability of signal detection. For multi-unit signal detection, the processor circuit 550 preferably harvests (e.g., senses and stores) many isolated neural signals from a cluster of multiple electrodes spaced to record independent signals (or alternatively from a single electrode).

The processor circuit 550 may further function to self-diagnose the neural interface system when implanted using the electrode signals or other sensor signals, such as to allow one to accurately identify noisy or shorted channel failures and help utilize the clustered electrode sites efficiently. The processor circuit 550 may include a single processing module. A module can include a combination of one or more of hardware circuits, firmware, and software to perform the functions described.

The essence of the signal processing problem is that neural signals distribute themselves on an array as: Y=AX+N, where Y represents the observed sensor signals, X represents the neural signal time series, A is the matrix of coefficients describing projections of the neural signals on the electrode array, and N represents the noise time series for each sensor channel having a covariance matrix K. Because neural signals are fairly compact in time, the processor circuit 550 may perform a method such as forming synchrony groups to determine the footprint of a neuron on the channels and later the weights within the footprint used in A. The processor circuit 550 may also calculate the covariance of N alone by removing obvious neural signals from the channels. The processor circuit 550 may then extract the neural signal time series X by using a pseudo inverse such as the Gauss-Markov equation.

In one variation, the processor utilizes the equation for the best linear unbiased estimator (BLUE) of $\hat{X}=(A^T K^{-1} A)^{-1} A^T K^{-1}$. The variance of $\hat{X}$ is $(A^T K^{-1} A)^{-1}$ and decreases as the number of observation channels increases. In another variation, the processor circuit 550 may perform independent component analysis (ICA) by rotating the signal space until independence in signals is achieved. Both the ICA and BLUE analyses result in a deconvolution filter. In particular, since the neural interface system preferably includes relatively large number of electrode site, the number of electrode sites or observation channels (i.e., rows of A) is large compared to the number of significant neurons (i.e., columns of A) and the ICA and BLUE analyses produce signals that are more reliable and free from interference. In an alternative embodiment, such as in a neural interface system with fewer electrode sites, the processor circuit 550 may augment the spatial signal space decomposition with wavelets or other signal decompositions suitable to neural signals, to increase the dimension of observation space, as would be readily understood by one ordinarily skilled in the art. However, any suitable signal processing methods may additionally and/or alternatively be used.

In another variation, the processor circuit 550 may use principle component analysis (PCA) to discriminate the multiple neural signals by wave shape, using expansion of the signals into a compact function space, the coefficients of which can be cluster cut into individual neural signals.

The system preferably further includes one or more interconnects and/or electrical subsystems, such as those described in U.S. Application number 2008/0208283 entitled "Neural Interface System", which is incorporated in its entirety by this reference.

Figure 8:
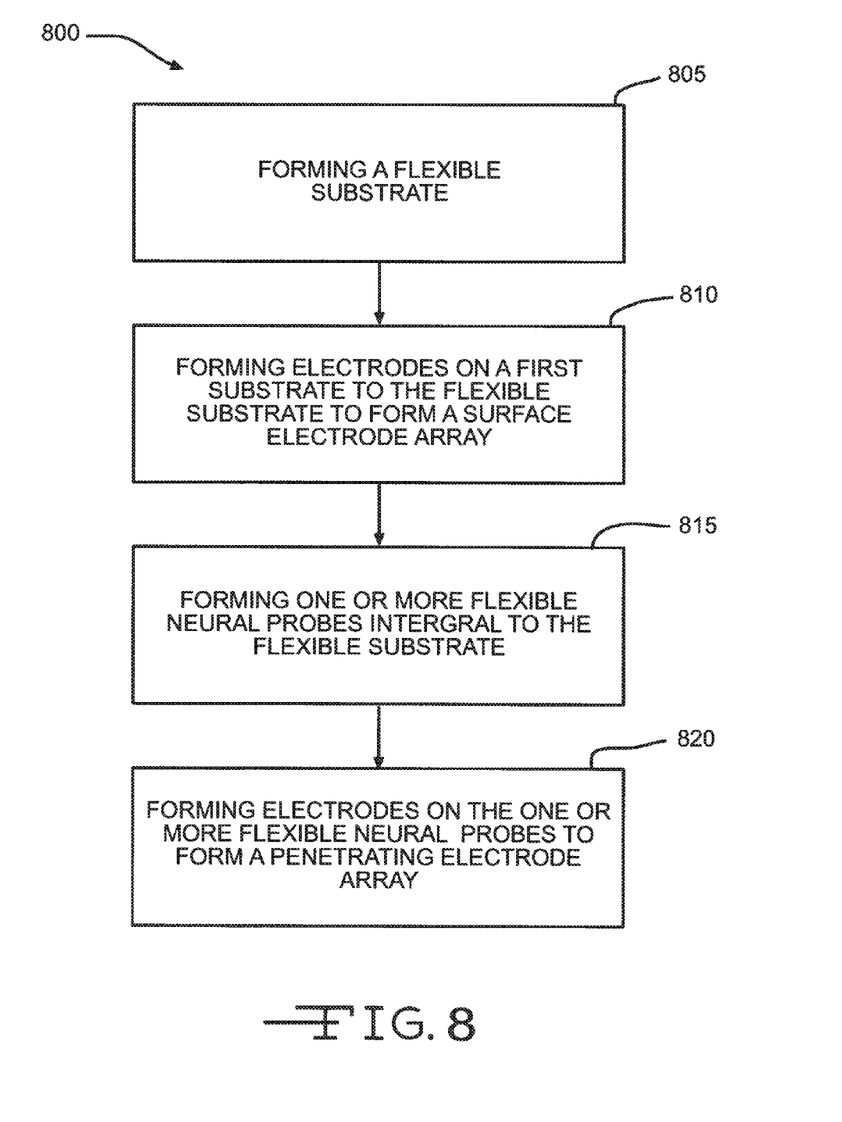
FIG. 8 is flow diagram of an example of a method of making a hybrid clustered neural interface system.

FIG. 8 is flow diagram of an example of a method of making a hybrid clustered neural interface system. At block 805, a flexible substrate is formed. In some examples, the flexible substrate is formed using a thin-film material. In certain examples, the thin-film material includes polyimide. In some examples, the flexible substrate is a monolithic substrate formed using the thin-film material. In some examples, the flexible substrate is formed by forming (e.g., bonding the thin-film substrate to a flexible backing At block 810, electrodes are formed on a first surface of the flexible substrate to form a surface electrode array. At block 815, one or more flexible neural probes are formed integral to the flexible substrate. In some examples, a flexible neural probe is formed by at least one of bending or folding a portion of the flexible substrate to form the flexible neural probe. The neural probes may extend substantially orthogonal to the first substrate surface; thereby forming a three-dimensional (3D) flexible substrate. In other words, the substrate and the probes can be formed from a single sheet of thin-film to form a 3D substrate.

At block 820, electrodes are formed on the one or more flexible neural probes to form a penetrating electrode array. The electrodes of the surface electrode array and the penetrating electrode array are configured by their shape, size, and material to one or both of receive a neural signal from a neural signal source and provide electrical stimulation energy to a neural stimulation target.

The examples of the systems described herein include advanced architectures and materials that are precisely engineered to minimize adverse tissue reactions, and the multi-scale and multi-modal recording electrode arrays provide an unprecedented mechanism to provide system-level and local signal information content while improving long-term signal quality.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. A neural interface system, comprising:
   a) a flexible substrate comprising a first substrate surface;
   b) a plurality of first electrodes disposed on the first substrate surface to thereby provide a surface electrode array;
   c) at least one flexible neural probe extending away from the flexible substrate at an angle with respect to the first substrate surface; and
   d) a plurality of second electrodes formed on the at least one neural probe to thereby provide a penetrating electrode array that is insertable into biological tissue,
   e) wherein the first electrodes of the surface electrode array and the second electrodes of the penetrating electrode array are respectively configured to at least one of receive a neural signal from a neural signal source and provide electrical stimulation energy to a neural stimulation target.

2. The neural interface system of claim 1, wherein a plurality of the electrodes of at least one of the surface electrode array and the penetrating electrode array are distributed to substantially align to a target neural cluster.

3. The neural interface system of claim I, wherein a spacing of at least one of the first and second electrodes of the respective surface electrode array and the penetrating electrode array is scaled to a spacing of a target neural cluster, which spacing facilitates separate receiving of a neural signal from a neural signal source and stimulation of a neural stimulation target.

4. The neural interface system of claim 3, wherein a switch circuit is electrically coupled to at least one of the plurality of first and second electrodes, and wherein the switch circuit is configured to selectively activate a subset of the first and second electrodes for at least one of separate receiving a neural signal from a neural signal source and stimulation of a neural stimulation target.

5. The neural interface system of claim. 1, wherein the at least one neural probe is foldable to change a first position of the penetrating electrode array relative to a second position of the surface electrode array.

6. The neural interface system of claim 1, wherein the flexible substrate includes a plurality of electrical conductors in electrical continuity with the first electrodes of the surface electrode array and the second electrodes of the penetrating electrode array, wherein any one of the electrical conductors is configured for at least one of receiving a neural signal from the first and second electrodes and providing electrical stimulation energy to the first and second electrodes.

7. The neural interface system of claim 1, wherein the flexible substrate includes at least one fluid channel configured to deliver fluid to at least one of the first substrate surface and the at least one flexible neural probe.

8. The neural interface system. of claim 1, wherein the at least one fluid channel is included within at least a portion of the at least one flexible neural probe.

9. The neural interface system of claim 1, wherein the flexible substrate includes at least one optical channel configured to deliver light to at least one of the first substrate surface and the at least one neural probe.

10. The neural interface system of claim 1, wherein the flexible substrate is monolithic and includes a flexible thin-film substrate.

11. The neural interface system of claim 1, wherein the flexible substrate includes a thin-film substrate mounted on a flexible backing.

12. The neural interface system of claim 1, wherein the flexible substrate includes at least one of:
   a) a first aperture configured to deliver a fluid to the first substrate surface; and
   b) a second aperture configured to deliver light radiating outwardly from the first substrate surface.

13. The neural interface system of claim 1, wherein the at least one neural probe comprises a plurality of flexible neural probes of different lengths.

14. The neural interface system of claim 1, wherein the at least one neural probe is generally planar.

15. The neural interface system of claim 1, wherein the at least one neural probe is cylindrical.

16. The neural interface system of claim 1, wherein the flexible substrate includes at least one aperture configured to receive the at least one flexible neural probe.

17. The neural interface system of claim 1 wherein the at least one neural probe comprises a plurality of flexible neural probes arranged along a perimeter of the flexible substrate.

18. The neural interface system of claim 12, wherein the flexible substrate includes a flexible thin-film substrate mounted onto a temporary backing that is more rigid than the flexible thin-film substrate, and wherein the temporary backing is removable after contact of the flexible substrate with biological tissue.

19. A method for providing a neural interface system, comprising the steps of:
   a) forming a flexible substrate comprising a first substrate surface;
   b) forming a plurality of first electrodes on the first substrate surface to thereby form a surface electrode array;
   c) forming at least one flexible neural probe extending away from the flexible substrate at an angle with respect to the first substrate surface; and
   d) forming a plurality of second electrodes on the at least one neural probe to thereby form a penetrating electrode array that is insertable into biological tissue, e) wherein the first electrodes of the surface electrode array and the second electrodes of the penetrating electrode array are configured to at least one of receive a neural signal from a neural signal source and provide electrical stimulation energy to a neural stimulation target.

20. The method of claim 19, wherein forming the at least one neural probe includes at least one of bending or folding a portion of the flexible substrate to thereby form a three-dimensional flexible substrate.

21. The method of claim 20, wherein forming the at least one neural probe includes:
   a) folding a portion of a first flexible neural probe of a first length extending away from the first substrate surface of the flexible substrate at a first angle; and
   b) folding a portion of a second flexible neural probe of a second length extending away from the first substrate surface of the flexible substrate at a second angle,
   c) wherein the first and second length are the same or different and the first and second angles are the same or different.

22. The method of claim 19, wherein forming the surface electrode array and the penetrating electrode array includes scaling a spacing of the respective first and second electrodes of at least one of the surface electrode array and the penetrating electrode array to a spacing of a target neural cluster, wherein the scale of the spacing of the first and second electrodes facilitates separate receiving of a neural signal from a neural signal source of the target neural cluster and stimulation of a neural stimulation target of the target neural cluster.

23. The method of claim 19, including electrically coupling a switch circuit to the at least one of plurality of first and second electrodes, wherein the switch circuit is configured to selectively activate a subset of the first and second electrodes for at least one of receiving a neural signal from a neural signal source and stimulation of a neural stimulation target.

24. The method of claim 19, including electrically connecting a plurality of electrical conductors to the first and second electrodes of the respective surface electrode array and penetrating electrode array, wherein any one of the electrical conductors is configured for at least one of receiving a neural signal signals from the first and second electrodes and providing electrical stimulation energy to the first and second electrodes.

25. The method of claim 19, including forming at least one fluid channel in the flexible substrate, wherein the fluid channel is configured to provide fluid to at least one of the first substrate surface and the flexible neural probe.

26. The method of claim 25, including forming the at least one fluid channel within at least a portion of the at least one flexible neural probe.

27. The method of claim 19, including forming at least one optical channel in the flexible substrate, wherein the optical channel is configured to deliver light to at least one of the first substrate surface and the flexible neural probe.

28. The method of claim 19, wherein forming the flexible substrate includes:
   a) forming a monolithic flexible thin-firm substrate; and
   b) forming features of the flexible thin-film substrate using photolithography.

29. The method of claim 19, wherein forming the flexible substrate includes mounting a thin-film substrate on a flexible backing.

30. The method of claim 19, wherein forming the flexible substrate includes mounting a flexible thin-film substrate onto a temporary backing more rigid than the flexible thin-film substrate, and wherein the temporary backing is removable after contact of the flexible substrate with biological tissue.

31. The method of claim 19, wherein forming the at least one neural probe includes forming a plurality of flexible neural probes of different lengths.

32. The method of claim 19, wherein forming the at least one neural probe includes forming at least one generally planar neural probe.

33. The method of claim 19, wherein forming the at least one neural probe includes forming at least one cylindrical neural probe.

34. The method of claim 19, including arranging a plurality of the flexible neural probes along a perimeter of the flexible substrate.

35. The method of claim 19, wherein forming the at least one neural probe includes attaching the neural probe to a lumen.

36. The method of claim 19, including forming an aperture in the flexible substrate, the aperture being configured to receive the at least one neural probe.

37. The method of claim 19, wherein forming the flexible substrate includes forming at least one of:
   a) a first aperture in the flexible substrate configured to deliver a fluid to the first substrate surface; and
   b) a second aperture in the flexible substrate configured to deliver light radiating outwardly from the first substrate surface.

38. The neural interface system of claim 1 wherein the at least one neural probe extends away from the flexible substrate at an angle that is substantially orthogonal to the first substrate surface.

39. The neural interface system of claim 1 wherein the plurality of second electrodes formed on the at least one neural probe is arranged in a cluster selected from the group consisting of a stereotrode, a tetrode, an octrode, and a polytrode.

40. The neural interface system of claim 3 wherein the spacing is from 15 μm to 40 μm.

41. The neural interface system of claim 18 wherein the second electrodes of the penetrating electrode array comprise from 10 to 300 receiving electrodes.

42. The neural interface system of claim 1 wherein the flexible substrate includes at least one aperture through which more than one flexible neural probe extends.

43. The neural interface system of claim 1 wherein the flexible substrate has a thickness of about 5 μm, or less.

44. The neural interface system of claim 1 wherein at least one neural probe has an open perforation configured to help anchor the neural probe in tissue.

45. A neural interface system, comprising:
   a) a flexible substrate comprising a first substrate surface spaced from a second substrate surface by a substrate thickness, wherein the flexible substrate includes at least one aperture through the thickness thereof;
   b) a plurality of first electrodes disposed on the first substrate surface to thereby provide a surface electrode array;
   c) at least one flexible neural probe extending through the aperture and away from the flexible substrate at an angle with respect to the first substrate surface; and
   d) a plurality of second electrodes formed on the at least one neural probe to thereby provide a penetrating electrode array that is insertable into biological tissue,
   e) wherein the first electrodes of the surface electrode array and the second electrodes of the penetrating electrode array are configured to at least one of receive a neural signal from a neural signal source and provide electrical stimulation energy to a neural stimulation target.

* * * * *